United States Patent [19]
Kress et al.

[11] Patent Number: 5,212,319
[45] Date of Patent: May 18, 1993

[54] INTERMEDIATES TO 4-AMINO-HEXAHYDROBENZ[CD]INDOLES AND PROCESSES THEREFOR

[75] Inventors: Thomas J. Kress, Indianapolis, Ind.; M. Robert Leanna, Mundelein, Ill.; Michael J. Martinelli; Barry C. Peterson, both of Indianapolis, Ind.

[73] Assignee: Eli Lilly and Company, Indianapolis, Ind.

[21] Appl. No.: 799,924

[22] Filed: Nov. 26, 1991

Related U.S. Application Data

[63] Continuation of Ser. No. 485,194, Feb. 26, 1990, abandoned.

[51] Int. Cl.$^5$ .................. C07D 209/50; C07D 209/56
[52] U.S. Cl. ..................................... 548/436; 548/425
[58] Field of Search .............................. 548/436, 425

[56] References Cited

U.S. PATENT DOCUMENTS

| | | | |
|---|---|---|---|
| 2,809,974 | 10/1957 | Kornfeld et al. | 548/436 |
| 3,575,989 | 8/1971 | Razdan et al. | 548/436 |
| 4,098,895 | 7/1978 | Habele et al. | 548/378 |
| 4,110,339 | 8/1978 | Bach et al. | 548/436 |
| 4,153,712 | 5/1979 | Habele et al. | 548/375 |
| 4,576,959 | 5/1986 | Flaugh | 548/436 |
| 4,745,126 | 5/1988 | Leander | 514/411 |
| 4,914,214 | 4/1990 | Vincent et al. | 548/492 |

FOREIGN PATENT DOCUMENTS

| | | |
|---|---|---|
| 148440 | 7/1985 | European Pat. Off. |
| 332968A1 | 9/1989 | European Pat. Off. |
| 745495 | 5/1956 | United Kingdom |
| 791805 | 6/1958 | United Kingdom |

OTHER PUBLICATIONS

Kuhlmeyer et al., "Total synthesis of (-)2-deoxytortamius", Tetra. Lett., 25(32) 3429-3432 (1984).
Schubert, "Aminoglyciside . . .", Liebig Ann Chem 1986, 2009-2052 (1986).
Semple et al., "Total Synthesis . . .", J. Am. Chem. Soc. 102, 2505-2510 (1980).
Schubert, "Total synthesis . . .", Angew Chem 96, 102-103 (1984).
Bucciarelli et al., "Optical resolution . . .", CA 103, 196024y (1985).
March, "Advanced Organic Chemistry . . .", McGraw-Hill, 1968, p. 81.
H. Sugihara et al., Chem. Pharm. Bull., 26, 394-404 (1978).
E. C. Kornfeld et al., J. Am. Chem. Soc., 78, 3087-3114 (1956).
L. Nedelec et al., J. Med. Chem., 26, 522-527 (1983).
R. C. Elderfield and H. A. Hageman, J. Org. Chem., 14, 605-637 (1949).
H. Suzuki and H. Tani, Chem. Letters, 2129-2130 (1984).
J. T. Rudesell et al., J. Org. Chem., 36, 3071-3076 (1971).
J. T. Carlock and M. P. Mack, Tet. Lett., 5153-5156 (1978).
Freemer and Mondron, Synthesis, Dec. 1974, p. 894.
R. Appel, Angew. Chem. Internat. Edit, 14, 801-811 (1975).
J. S. Yadav and S. V. Mysorekar, Synth. Comm., 19, 1057-1060 (1989).
M. R. Leanna et al., Tet. Lett., 30, 3935-3938 (1989).
Flaugh, J. Med. Chem., 31, 1746 (1988).
T. W. Greene, Chapter 7, Protective Groups in Organic Synthesis.
J. W. Barton, Chapter 2, Protective Groups in Organic Chemistry.
Nichols, Org. Pre. and Proc. Int., 9, 277 (1977).
Mitsunobu, Synthesis, Jan. 1981, p. 1.
Sugi et al., Bull. Chem. Soc. Jap., 43, p. 1489 (1970).

Primary Examiner—C. Warren Ivy
Assistant Examiner—Celia Chang
Attorney, Agent, or Firm—Nancy J. Harrison; Leroy Whitaker; David E. Boone

[57] ABSTRACT

New intermediates, and processes therefor, provide an efficient method for deriving 4-amino-1,2,-2a,3,4,5-hexahydrobenz[cd]indoles, which are themselves intermediates to useful CNS agents, from the Kornfeld-Woodward ketone and like compounds. Preferred embodiments provide means for the preparation of substantially pure enantiomers of the desired 4-amino-1,2,2a,3,4,5-hexahydrobenz[cd]indole.

6 Claims, No Drawings

INTERMEDIATES TO 4-AMINO-HEXAHYDROBENZ[CD]INDOLES AND PROCESSES THEREFOR

This application is a continuation of application Ser. No. 07/485,194, filed on Feb. 26, 1990, now abandoned.

FIELD OF THE INVENTION

This invention relates to the fields of synthetic organic chemistry and pharmaceutical chemistry and provides valuable processes and intermediates to 4-amino-1,2, 2a,3,4,5-hexahydrobenz[cd]indoles, which are intermediates to compounds useful for the treatment of individuals suffering from or susceptible to various disorders of the central nervous system.

BACKGROUND OF THE INVENTION

The 4-amino-1,2,2a,3,4,5-hexahydrobenz[cd]indoles are useful intermediates to a number of valuable compounds. For example, Bach and Kornfeld, U.S. Pat. No. 4,110,339, disclose that 4-(di-n-propyl)amino-1,3,4,-5-tetrahydrobenz[cd]indole, useful as a prolactin inhibitor and in the treatment of Parkinsonism, is readily prepared from 1-benzoyl-4-amino-1,2,2a,3,4,5-hexahydrobenz[cd]indole. Additionally, Flaugh, U.S. Pat. No. 4,576,959, discloses a family of 6-substituted-4-dialkylamino-1,3, 4,5-tetrahydrobenz[cd]indoles, useful as antidepressive agents and as anxiolytic agents (as disclosed by Leander, U.S. Patent No. 4,745,126), some of which were prepared from substituted 4-amino-1,2,2a,-3, 4,5-hexahydrobenz[cindoles. In both of these inventions, the desired intermediates were prepared via circuitous routes from the Kornfeld-Woodward ketone, Kornfeld et al., J. Am. Chem. Soc., 78, 3087 (1956):

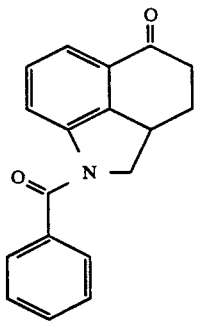

I

Furthermore, Glaser et al., EPO 148,440, disclose another series of 6-substituted-4-amino-1,3,4,5-tetrahydrobenz[cd]indoles. Flaugh, et al., J. Med. Chem., 31, p.p. 1746–1753 (1988) teach a method of preparing the 6-methoxy compound of Glaser et al. which utilizes 4-amino-6-methoxy-1,2,2a,3,4,5-hexahydroben[cd]indole.

This invention provides intermediates and processes for efficiently deriving 4-amino-1,2,2a,3,4,5-hexahydrobenz[cd]indoles from the Kornfeld-Woodward ketone. A preferred embodiment of the invention provides intermediates and processes for a stereospecific synthesis of 4-amino-1,2,2a,3,4,5-hexahydrobenz[cd]indoles.

SUMMARY OF THE INVENTION

This invention provides compounds of the formula

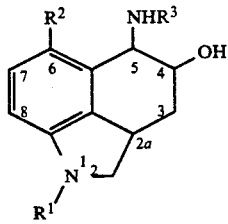

III wherein $R^1$ is hydrogen or an amino-protecting group; $R^2$ is hydrogen, halo, hydroxy, carboxy, $C_1$–$C_4$ alkoxy, $C_1$–$C_4$ alkylthio, $C_1$–$C_4$ alkoxycarbonyl, cyano, aminocarbonyl, or aminocarbonyl substituted with one or two $C_1$–$C_4$ alkyl groups; and $R^3$ is hydrogen, or is $C_1$–$C_4$ alkyl or is $C_1$–$C_4$ alkyl substituted with one to three groups selected from halo, nitro, or phenyl substituted with zero to two groups selected from hydroxy, methyl, nitro, or halo. This is with the proviso that the 4-and 5-positions are both in the R configuration or are both in the S configuration.

This invention further provides compounds of the formula

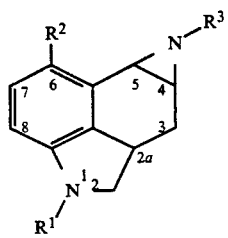

IV provided that if the 4-position is in the R configuration, the 5-position is in the S configuration, and provided that if the 4-position is in the S configuration, the 5-position is in the R configuration.

Additionally, this invention provides a process for preparing compounds of Formula IV, which comprises the reaction of a compound of Formula III with 1) a tertiary amine of the formula $(R^4)_3N$, where the $R^4$ groups are independently $C_1$–$C_4$ alkyl, and 2) with methanesulfonyl chloride.

Finally, this invention provides a stereospecific process for preparing a compound which is a substantially pure enantiomer of the formula

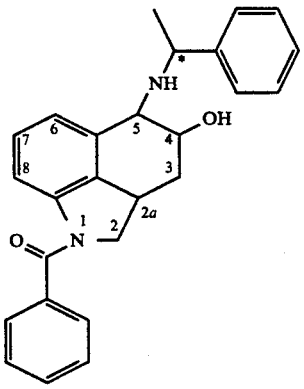

wherein i) the 2-a carbon is in the R configuration, the 4 carbon is in the R configuration, the 5 carbon is in the R configuration; and the carbon marked * is in the S configuration; or ii) the 2-a carbon is in the S configuration, the 4 carbon is in the S configuration, the 5 carbon is in the S configuration, and the carbon marked * is in the R configuration; or iii) the 2-a carbon is in the R configuration, the 4 carbon is in the S configuration, the 5 carbon is in the S configuration, and the carbon marked * is in the R configuration;

iv) the 2-a carbon is in the S configuration, the 4 carbon is in the R configuration, the 5 carbon is in the R configuration, and the carbon marked * is in the S configuration;

which comprises:

1) reaction of a mixture of substantially the α-isomers or substantially the β-isomers of the formula

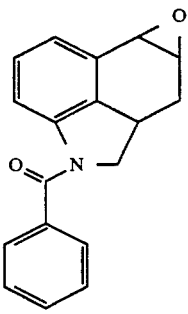

with a substantially pure enantiomer of 1-phenylethylamine, in n-butanol, and 2) selective crystallization from n-butanol.

DESCRIPTION OF THE PREFERRED EMBODIMENTS

All temperatures in this document are expressed in degrees Celsius. All proportions such as percentages, ratios, and the like are expressed in weight proportions, except for mixtures of solvents which are expressed in volume proportions, and except as otherwise noted.

The various terms used in structural formulae in this document are used in a manner conventional in the art of organic chemistry. For example, $C_1$–$C_4$ alkyl includes methyl, ethyl, propyl, isopropyl, butyl, s-butyl, isobutyl, and t-butyl; $C_1$–$C_4$ alkoxy includes methoxy, ethoxy, propoxy, isopropoxy, butoxy, isobutoxy, and t-butoxy; $C_1$–$C_4$ alkylthio includes methylmercapto, ethyl-mercapto, propylmercapto, isopropylmercapto, butyl-mercapto, isobutylmercapto, and t-butylmercapto; $C_1$–$C_4$ alkoxycarbonyl includes methoxycarbonyl, ethoxycarbonyl, propoxycarbonyl, isopropoxycarbonyl, butoxycarbonyl, isobutoxycarbonyl, and t-butoxycarbonyl; and halo includes fluorine, chlorine, bromine and iodine.

The term amino-protecting group is used as it is frequently used in synthetic organic chemistry, to refer to a group which will prevent an amino group from participating in a reaction carried out on some other functional group of the molecule, but which can be removed from the amine when it is desired to do so. Such groups are discussed by T. W. Greene in chapter 7 of *Protective Groups in Organic Synthesis,* John Wiley and Sons, N.Y., 1981, and by J. W. Barton in chapter 2 of *Protective Groups in Organic Chemistry,* J. F. W. McOmie, ed., Plenum Press, New York, 1973, which are incorporated herein by reference in their entirety. Examples of such groups include those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; benzyl and substituted benzyl such as 3,4-dimethoxybenzyl, o-nitrobenzyl, and triphenyl-methyl; acyl and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, and p-toluenesulfonylamino-carbonyl.

It will be recognized that compounds of Formulae III and IV contain three chiral centers at the 2a-, 4-, and 5-positions, in addition to those chiral centers which might exist in the substituents $R^1$, $R^2$, and $R^3$. This invention provides all the stereoisomers of compounds of Formula III, whether in mixtures or in substantially pure form, provided that the 4- and 5-positions are either both R or both S. This invention provides all the stereoisomers of compounds of Formula IV, whether in mixtures or in substantially pure form, provided that if the 4-position is R, the 5-position is S, and provided that if the 4-position is S, the 5-position is R.

While all the embodiments of the invention are useful and valuable, certain embodiments are particularly preferred. The preferred limitations are discussed below. It will be understood that further, more limited aspects of the invention are described by combining limitations set forth below.

This invention is particularly valuable when $R^3$ contains at least one chiral center. Such a substituent is often referred to in the art of synthetic organic chemistry as a chiral auxiliary and, as will be shown, is useful for stereospecific syntheses of intermediates and products from racemic mixtures of starting materials. Therefore, preferred embodiments of compounds of Formula III and IV are these in which $R^3$ contains at least one chiral center in substantially a single stereoisomeric configuration. Preferred embodiments of the processes of this invention are those which prepare such compounds.

In the compounds of this invention and in the processes provided by this invention, preferred values of $R^3$ are n-propyl, isopropyl, benzyl, and 1-(p-nitrophenyl)ethyl and 1-phenylethyl, the most highly preferred being the substantially pure stereochemical configurations of 1-phenylethyl. Preferred values of $R^2$ are hydrogen, methoxy, aminocarbonyl, cyano, methoxycarbonyl, ethoxycarbonyl, bromo, and iodo; the most highly preferred value of $R^2$ is hydrogen. Finally, preferred values of $R^1$ are hydrogen, benzoyl, acetyl, trichloroacetyl, trifluoroacetyl, or p-toluenesulfonyl; the most highly preferred value of $R^1$ is benzoyl.

The following list of compounds of Formula III are set forth to ensure the reader's understanding of the invention. It is not a complete list of included compounds and is not to be construed as limiting the scope of the invention. Each of the following compounds has at least 3 chiral centers. It will be understood that each named compound is intended to designate all of the possible stereoisomers, whether in mixtures or in substantially pure form, provided that the two centers at the 4- and 5-positions are both R or both S.

1-benzoyl-4-hydroxy-5-(1-phenylethyl)amino-6-bromo-1,2, 2a,3,4,5-hexahydrobenz[cd]indole 1-trichloroacetyl-4-hydroxy-5-(n-propyl)amino-6-dimethylaminocarbonyl-1, 2,2a,3,4,5-hexahydrobenz[cd]indole 1-(t-butoxy)carbonyl-4-hydroxy-5-(t-butyl)-amino-6-methoxy-1, 2,2a,3,4,5-hexahydrobenz[cd]indole 1-benzyl-4-hydroxy-5-(2-chlorobutyl)amino-6-methylmercapto-1, 2,2a,3,4,5-hexahydrobenz[cd]indole 4-hydroxy-5-amino-1,2,2a,3,4,5-hexahydrobenz-[cd]indole 1-formyl-4-hydroxy-5-(1-(4-nitrophenyl)ethyl)-amino-6-ethoxy-1, 2,2a,3,4,5-hexahydrobenz[cd]indole 1-benzyloxycarbonyl-4-hydroxy-5-(2-(3,4-dichlorophenyl) ethyl)amino-6-iodo-1,2,2a,3,4,5-hexahydrobenz[cd]indole 1-(2,2,2-trichloroethoxy)carbonyl-4-hydroxy-5-bromochloromethylamino-6-acetyl-1, 2,2a,3,4,5-hexahydrobenz[cd]indole 1-(p-toluenesulfonyl)-4-hydroxy-5-(1-(2-cloro-4-cyanophenyl) propyl)amino-6-hydroxy-1,2,2a,3,4,5-hexahydrobenz[cd]indole 1-(p-bromophenylsulfonyl)-4-hydroxy-5-(p-nitrobenzyl)amino-6-ethylmercapto-1, 2,2a,3,4,5-hexahydrobenz[cd]indole 1-allyloxycarbonyl-4-hydroxy-5-(1-hydroxy-ethyl)amino-6-fluoro-1, 2,2a,3,4,5-hexahydrobenz[cd]indole 1-triphenylmethyl-4-hydroxy-5-amino-1,2,2a,3,-4, 5-hexahydrobenz[cd]indole 1-(1-methyl-1-phenylethoxy)carbonyl-4-hydroxy-5-isopropylamino-6-methylaminocarbonyl-1, 2,2a,3,4,5-hexahydrobenz[cd]indole 1-benzoyl-4-hydroxy-5-(1-phenylethyl)amino-1, 2,2a,3,4,5-hexahydrobenz[cd]indole 1-benzoyl-4-hydroxy-5-(1-(4-nitrophenyl)ethyl)-amino-6-iodo-1, 2,2a,3,4,5-hexahydrobenz[cd]indole 1-phenoxyacetyl-4-hydroxy-5-(1-phenylpropyl)-amino-6-cyano-1, 2,2a,3,4,5-hexahydrobenz[cd]indole The following list of compounds of Formula IV are set forth to ensure the reader's understanding of the invention. It is not to be construed as limiting the scope of the invention. Each of the following compounds has at least 3 chiral centers. It will be understood that each named compound is intended to designate all of the possible stereoisomers, whether in mixtures or in substantially pure form.

1-benzoyl-4,5-(1-phenylethyl)azirino-6-bromo-1, 2,2a,3,4,5-hexahydrobenz[cd]indole 1-trichloroacetyl-4,5-(n-propyl)azirino-6-dimethylaminocarbonyl-1, 2,2a,3,4,5-hexahydrobenz[cd]indole 1-(t-butoxy)carbonyl-4,5-(t-butyl)azirino-6-methoxy-1, 2,2a,3,4,5-hexahydrobenz[cd]indole 1-benzyl-4,5-(2-chlorobutyl)azirino-6-methyl-mercapto-1, 2,2a,3,4,5-hexahydrobenz[cd]indole 4,5-azirino-1,2,2a,3,4,5-hexahydrobenz[cd]-1-formyl-4,5-(1-(4-nitrophenyl)ethyl) azirino-6-ethoxy-1,2,2a,3,4,5-hexahydrobenz[cd]indole 1-formyl-4,5-(1-(4-nitrophenyl)ethyl)azirino-b 6-ethoxy-1, 2,2a,3,4,5-hexahydrobenz[cd]indole 1-benzyloxycarbonyl-4,5-(2-(3,4-dichloro-phenyl)ethyl)azirino-6-iodo-1, 2,2a,3,4,5-hexahydrobenz-cd]indole 1-(2,2,2-trichloroethoxy)carbonyl-4,5-bromochloromethylazirino-6-acetyl-1, 2,2a,3,4,5-hexahydrobenz-cd]indole 1-(p-toluenesulfonyl)-4,5-(1-(2-chloro-4-cyano-phenyl) propyl)azirino-6-hydroxy-1,2,2a,3,4,5-hexahydrobenz[cd]indole 1-(p-bromophenylsulfonyl)-4,5-(p-nitrobenzyl)-azirino-6-ethylmercapto-1, 2,2a,3,4,5-hexahydrobenz[cd]indole 1-allyloxycarbonyl-4,5-(1-hydroxyethyl)azirino-fluoro-1, 2,2a,3,4,5-hexahydrobenz[cd]indole 1-triphenylmethyl-4,5-azirino-1,2,2a,3,4,5-hexahydrobenz[cd]indole 1-(1-methyl-1-phenylethoxy)carbonyl-4,5-isopropylazirino-6-methylaminocarbonyl-1, 2,2a,3,4,5-hexahydrobenz[cd]indole 1-benzoyl-4,5-(1-phenylethyl)azirino-1,2,2a,-3, 4,5-hexahydrobenz[cd]indole 1-benzoyl-4,5-(1-(4-nitrophenyl)ethyl)azirino-6-iodo-1, 2,2a,3,4,5-hexahydrobenz[cd]indole 1-phenoxyacetyl-4,5-(1-phenylpropyl)azirino-6-cyano-1, 2,2a,3,4,5-hexahydrobenz[cd]indole Synthesis Scheme I illustrates the preparation of the compounds of this invention and the use of those compounds as intermediates.

Epoxides of Formula II are known to the art or can be prepared from compounds known to the art using common reagents and techniques. For example, Flaugh, et al., J. Med. Chem., 31, 1746 (1988); Nichols et al.,

SCHEME I

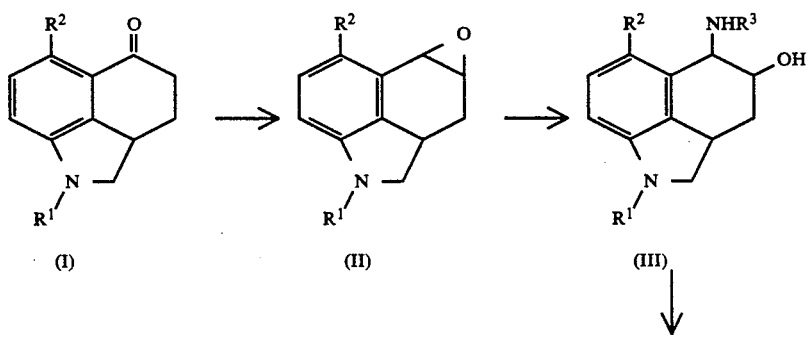

SCHEME I
-continued

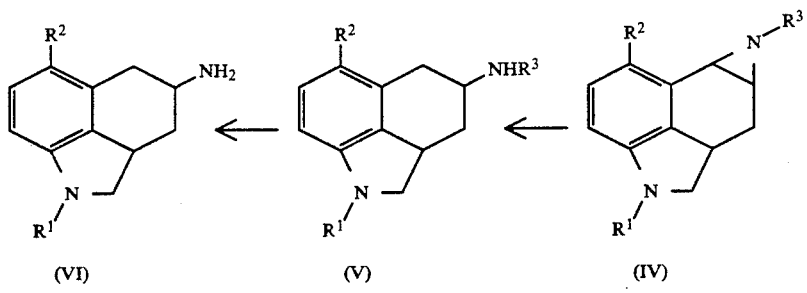

Org. Prep. and Proc., Int., 9, 277 (1977); and Leanna et al., Tet. Lett., 30, No. 30, 3935 (1989), teach methods of preparation of various embodiments of compounds of Formula II. Those skilled in the art of organic chemistry will recognize that there are four stereoisomers of Formula II:

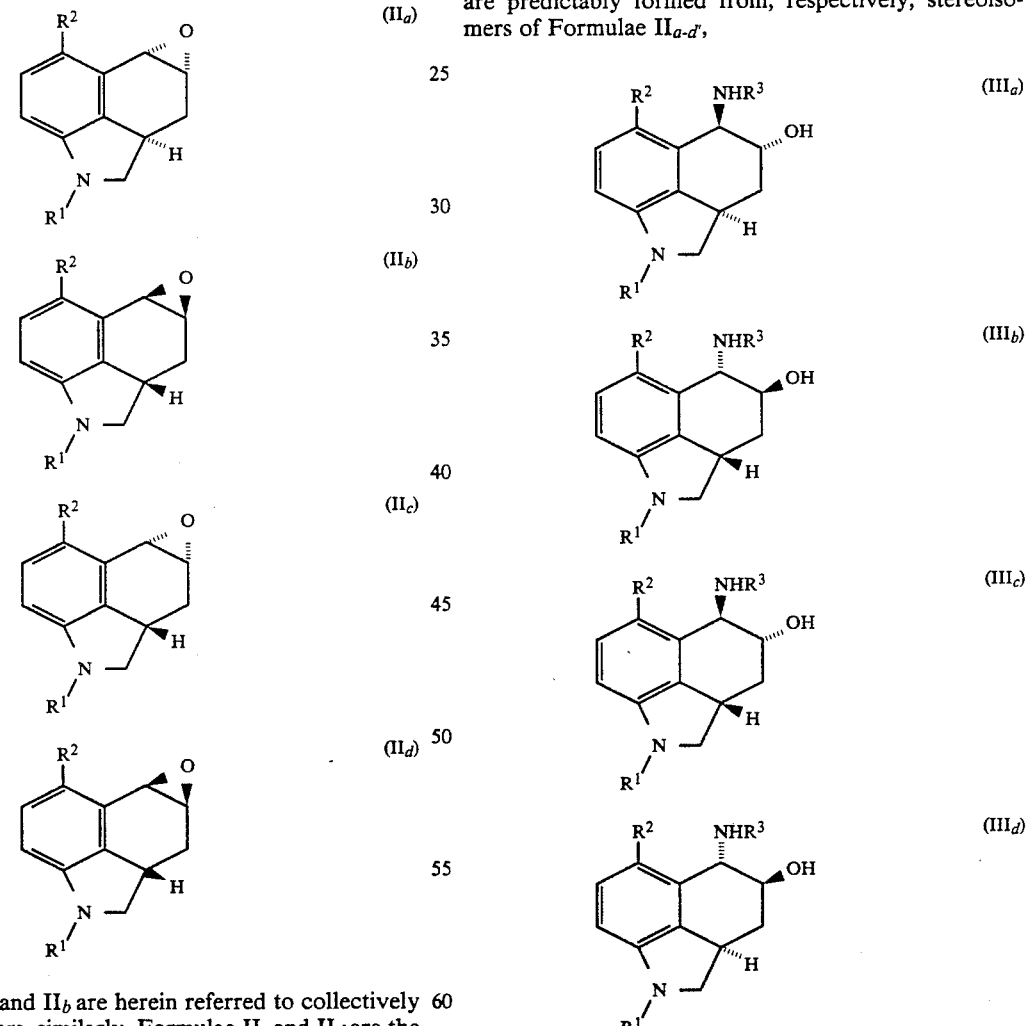

Formulae $II_a$ and $II_b$ are herein referred to collectively as the α-isomers; similarly, Formulae $II_c$ and $II_d$ are the β-isomers. Leanna et al., supra, teach the preparation of epoxides of Formula II which are substantially α or substantially β, as desired. The preferred starting material is the compound of Formula II wherein $R^1$ is benzoyl and $R^2$ is hydrogen; the most preferred starting material is the mixture of substantially the α-isomers thereof.

Amino alcohols of Formula III are formed by reacting an epoxide of Formula II with an amine of formula $R^3NH_2$. Such amines are readily available. Opening of the epoxide ring proceeds substantially regiospecifically with the amino group at the 5-position and the hydroxyl group at the 4-position. The reaction is also stereospecific in the sense that stereoisomers of Formulae IIIa-d are predictably formed from, respectively, stereoisomers of Formulae $II_{a-d'}$, A stereoselective synthesis of the amino alcohol of Formula III, and hence of all the subsequent intermediates and products of Scheme I, can be effected by utilizing a substantially pure enantiomer of an amine of the formula $R^3NH_2$ wherein $R^3$ contains at least one chiral center. The diastereomers of the resulting amino alcohol can then be separated by a number of means known in the art, for example by chromatography or crystallization. Suitable solvents for recrystallization include those such as diethyl ether, n-butanol, and mixtures of hexane and ethyl acetate. An alternative method of achieving a stereospecific synthesis comprises conversion of all the diastereomers of Formula III to corresponding diastereomers of Formula IV, followed by the separation of said diastereomers of Formula IV; that alternative method is discussed below. If a stereoselective synthesis is not desired, then no means of separation of the stereoisomers of the amino alcohol of Formula II is required and the amine $R^3NH_2$ need not be optically active.

A particularly efficient stereoselective process for a highly preferred compound of Formula III, 1-benzoyl-4-hydroxy-5(1-pnenylethyl)amino-1,2,2a,3,4,5-hexahydrobenz[cd]indole, comprises the reaction of a mixture of substantially the α-isomers of the corresponding epoxide of Formulae II, or a mixture of substantially the β-isomers of the corresponding epoxide of Formula II, with a substantially pure enantiomer of 1-phenethylamine in the solvent n-butanol and the subsequent selective crystallization of one of the two isomers of the amino alcohol. The temperature of the reaction can be from about 50° to about 150°, preferably about 80° to about 100°.

After the reaction is complete, as determined for example by thin layer chromatography or liquid chromatography, the desired amino alcohol is crystallized at about −20° to about 40°; the preferred temperature for the crystallization is about 0° to about 15°. Therefore this process has the valuable attribute that the reaction and the separation of stereoisomers occur efficiently in a single step. By the proper selection of the epoxide isomers, α or β, and the enantiomer of 1-phenylethylamine, R or S, one can determine which of the stereoisomers of the compound of Formula III will precipitate from the reaction mixture. For example, a preferred stereoisomer of 1-benzoyl-4-hydroxy-5-(1-phenylethyl) amino-1,2,2a,3,4,5-hexahydrobenz[cd]indole, the (2a-R,4-R,5-R)-isomer, can be selectively prepared by reacting the α-epoxides with S-1-phenylethylamine.

A number of methods of forming aziridines such as those of Formula IV from amino alcohols such as those of Formula III are known to the art. Two examples are the use of diethyl azodicarboxylate and triphenylphosphine (O. Mitsunobu, *Synthesis*, Jan., 1981, page 1), and the use of bromine and triphenylphosphine (J. P. Freemer and P. J. Mondron, *Synthesis*, Dec., 1974, page 894).

This invention provides a particularly efficient alternative to the above methods. A compound of Formula III is treated with a tertiary amine in an inert solvent followed by the addition of methanesulfonyl chloride. The following stereoisomers of the aziridine of Formula IV, IV$_{a-d}$, arise respectively from the stereoisomers of Formula III$_{a-d}$, with retention of configuration at any chiral center in the substituents $R^1$, $R^2$ or $R^3$ as well as at position 2a:

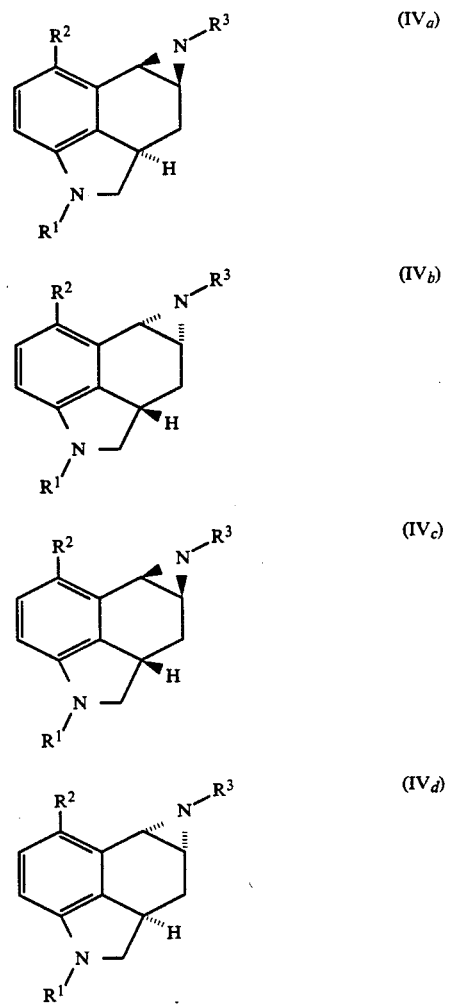

Suitable tertiary amines are those of the formula $(R^4)_3N$, where the $R^4$ groups are independently $C_1$-$C_4$ alkyl. Suitable solvents are chlorinated hydrocarbons such as methylene chloride, chloroform, carbon tetrachloride, and dichloroethane; aromatic hydrocarbons such as benzene, toluene, and the xylenes; and ethers such as tetrahydrofuran, diethyl ether, and methyl t-butyl ether. The reaction can be conducted at a temperature from about −35° to about 45°. In the preferred embodiment, the amino alcohol is treated with triethylamine in methylene chloride at about −20° to about 0°, then the reaction mixture is warmed to about 15° to about 35° for the completion of the reaction. If desired, the product, an aziridine of Formula IV, can be crystallized from an appropriate solvent such as acetonitrile or isopropanol after an aqueous workup. In the event that $R^3$ contains at least one chiral center in substantially a single stereoconfiguration and that the aziridine of Formula IV is prepared as a mixture of stereoisomers, said stereoisomers may be separated by methods such as chromatography and crystallization, thereby providing a stereospecific synthesis of the aziridine of Formula IV and subsequent products.

The aziridine ring can be opened to form an intermediate secondary amine of Formula V. A number of methods of opening aziridines are commonly known. It is, however, crucial that the method utilized for opening the aziridine to form a secondary amine of Formula V be substantially regiospecific; the aziridine must be opened to form substantially the 4-amino compound rather than the 5-amino compound. One such method is catalytic hydrogenolysis as taught by Y. Sugi and S. Mitsui, *Bull. Chem. Soc. Jap.*, 43, pp. 1489-1496 (1970). Catalysts which are suitable are the usual hydrogenation and hydrogenolysis catalysts, such as the noble metal catalysts; the preferred catalyst is palladium. Suitable solvents include hydrocarbons such as hexanes and heptanes; aromatic hydrocarbons such as benzene, toluene, xylenes, ethylbenzene, and t-butylbenzene; alcohols such as methanol, ethanol, and isopropanol; and mixtures of solvents such as acetic acid mixed with said alcohols. The preferred solvent for preparing the compound of Formula V, wherein $R^1$ is benzoyl, $R^2$ is hydrogen, and $R^3$ is 1-phenylethyl, is a mixture of methanol and acetic acid. The source of hydrogen may be an atmosphere of elemental hydrogen supplied at a pressure of about 1 atmosphere or higher, or the source of hydrogen may be compounds which are suitable to serve as hydrogen donors in a catalytic transfer hydrogenolysis reaction, such as formic acid, hydrazine, or cyclohexene. The preferred hydrogen source is an atmosphere of hydrogen gas supplied at about 1 to about 10 atmospheres pressure. The temperature of the reaction may be from about $-20°$ to about $80°$; the preferred temperature for the hydrogenolysis of the aziridine wherein $R^1$ is benzoyl, $R^2$ is hydrogen, and $R^3$ is 1-phenylethyl is about $-20°$ to about $0°$.

The conversion of compounds of Formula IV to compounds of Formula V proceeds without disturbing the stereochemical configuration of the chiral centers at the 2a- or 4- positions of the Formula V or of the chiral centers that may be present in any of the substituents.

If desired, the compound of Formula V can be isolated by the usual methods such as crystallization. The secondary amine of Formula V can be converted to a primary amine of Formula VI by a number of methods known to the art of organic chemistry, or alternatively the secondary amine itself can be used as an intermediate to valuable compounds without conversion to the primary amine.

However, the preferred method is to convert the secondary amine of Formula V to the primary amine of Formula VI without isolating the secondary amine, but rather by simply continuing without interruption the hydrogenolysis reaction that produced the compound of Formula V. Therefore, the preferred solvent and catalyst are the same as those for the preparation of the secondary amine of Formula V. It may be desirable to conduct the hydrogenolysis of the secondary amine of Formula V at a different temperature or a different pressure or different temperature and pressure than the hydrogenolysis of the aziridine of Formula IV. For the hydrogenolysis of the preferred compound of Formula V wherein $R^1$ is benzoyl, $R^2$ is hydrogen, and $R^3$ is 1-phenylethyl, the preferred temperature and pressure are about $50°$ to about $60°$ and about 1 to about 20 atmospheres.

The hydrogenolysis of compounds of Formula V to compounds of Formula VI proceeds without disturbing the stereochemical configuration of the chiral centers at the 2a- or 4- positions.

The isolation of the compound of Formula VI can be accomplished by the usual methods such as crystallization. If desired, the compound of Formula VI can be further purified, for example by recrystallization.

Of course, as those skilled in the art will recognize, variations of Scheme I will be desirable or necessary for certain embodiments of the invention. For example, it may be undesirable to subject a compound in which $R^2$ is halo to the catalytic hydrogenolysis steps of Scheme I, because the undesired displacement of the halogen may compete with the desired hydrogenolysis of the carbon-nitrogen bonds. One alternative strategy is to postpone the halogenation until after the hydrogenolysis. Another alternative strategy is to utilize a milder means of reduction that would leave the halogen in place. A third alternative, useful in the instance when the halogen is to serve as a leaving group, is to perform the desired displacement of halogen before the hydrogenolysis step.

Compounds of Formula VI have been demonstrated to be useful intermediates to other valuable compounds. For example, Bach and Kornfeld, U.S. Pat. No. 4,110,339, prepared 4-(di-n-propyl)amino-1,3,4,5-tetrahydrobenz[cd]indole, useful for the treatment of conditions in which an excess of prolactin is present, from the compound of Formula VI in which $R^1$ is benzoyl and $R^2$ is hydrogen by alkylation of the amino group, hydrolysis of the benzoyl group, and oxidation of the five-membered ring. Flaugh, U.S. Pat. No. 4,576,959, discloses 6-substituted-4-dialkylamino-1,3,4,5-tetrahydrobenz[cd]indoles, useful as antidepressive agents, and methods for their preparation from compounds such as those of Formulae V and VI. Flaugh's compounds include those substituted at the 6-position with halogen, cyano, aminocarbonyl, amino, and nitro. Glaser et al., EPO 0148440, disclose compounds, with $C_1$-$C_4$ alkoxy and $C_1$-$C_4$ alkylthio substituents at the 6-position, which may be prepared from compounds of Formula V or VI in which $R^2$ is $C_1$-$C_4$ alkoxy or $C_1$-$C_4$ alkylthio. For example, Flaugh et al., *J. Med. Chem.*, 31, pp. 1746-1753 (1988), teach the preparation of 4-(di-n-propyl)amino-6-methoxy-1,3,4,-5-tetrahydrobenz[c-d]indole from the corresponding compound of Formula VI in which $R_2$ is methoxy. Compounds of Flaugh, of Bach and Kornfeld, and of Glaser et al. which are substantially pure enantiomers may be prepared from compounds of Formula V or VI which are substantially pure enantiomers using the methods of Flaugh, the methods of Flaugh et al., the methods of Bach and Kornfeld, or other methods known to the art. Therefore, compounds of Formulae V and VI are useful for the preparation of a variety of valuable compounds.

The following examples illustrate the preparation and use of the processes and intermediates provided by this invention. The preparation which follows the examples illustrates the use of this invention in providing the most preferred tetrahydrobenz[cd]indole.

EXAMPLE 1

(2a-R,4-R,5-R)-1-Benzoyl-4-hydroxy-5-(S-1-phenylethylamino-1, 2,2a,3,4,5-hexahydrobenz[cd]indole A charge of (2a-RS,2a-α,4-α,5-α)-1-benzoyl-4,-5-epoxy-1, 2,2a,3,4,5-hexahydrobenz[cd]indole (482.5 g, 1.74 moles) was dissolved in n-butanol (4400 mL) and split into two 5000-ml three-neck flasks, each one equipped with a mechanical stirrer, a thermocouple and a condenser topped with a nitrogen inlet. The (S)-1-phenylethylamine (900 ml total; 450 ml, 6.98 moles to each flask) was added and the solution was stirred at 90° overnight. A small aliquot was taken and the n-butanol was removed in vacuo for thin layer chromatography (SiO₂, 1:1 hexanes:ethyl acetate) which showed no starting material after 24 hours. The reaction mixture was allowed to cool to room temperature, whereupon the desired amino alcohol crystallized directly from the reaction mixture. The crystalline material was filtered, washed with diethyl ether (2000 ml for each section), and dried. The first crop, both sections combined, was 168.26 g of the desired product and was used directly in the subsequent reaction. A second crop was obtained by evaporation of the above filtrates to dryness, dissolution in toluene (200 ml), and the addition of hexanes (100 ml) and diethyl ether (100 ml). The resulting solution was allowed to stand in the refrigerator overnight to provide an additional 39.2 g of the desired product after filtration. The crystalline material was analyzed and provided the following data.

PHYSICAL DATA:
m.p.: 158°–160°
IR: 3480 (br), 1638 (s), 1610 (w), 1470 (s), 1457 (s), 1394 (s) cm$^{-1}$.
NMR: ($^1$H, ppm, CDCl₃): 7.02–7.56 (m, 13H), 4.21 (q, 1H, J=6.6 Hz), 4.25 (br s, 1H), 3.63 (m, 2H), 3.42 (m, 2H), 2.72 (br s, 1H, exchanges with D₂O), 1.99 (m, 1H), 1.80 (m, 1H), 1.47 (d, 3H, J=6.6 Hz).
M.S.: m/e=398, 355, 249, 145, 105.
U.V.: $\lambda_{max}$=292 ($\epsilon$=8930), 265 ($\epsilon$=11400) in ethanol.
TLC: $R_f$=0.68 (SiO₂, 42:42:16 ethyl acetate:hexane:triethylamine)=desired diastereomer
$R_f$=0.62 (SiO₂, 42:42:16 ethyl acetate:hexane:triethylamine)=undesired diastereomer
$R_f$=0.36 (SiO₂, hexane:ethyl acetate 1:1)=amino alcohols (mixture).

| Analysis | C | H | N |
|---|---|---|---|
| theory | 78.37 | 6.58 | 7.03 |
| found | 78.14 | 6.67 | 6.77 |

$[\alpha]_D$= −37.58° (589 nm).

EXAMPLE 2

(2a-R,4-S,5-R)-1-Benzoyl-4,5-(S-1-phenylethyl)azirino-1,2,2a,3,4,5-hexahydrobenz[cd]indole Example 2A: A solution of the compound prepared by the method of Example 1 (749.5 g) in methylene chloride (6000 ml) was cooled to −10° under an atmosphere of nitrogen. Triethylamine (590 g, 3.1 equiv) was then added to the mixture, followed by the dropwise addition of methanesulfonyl chloride (330 g, 1 5 equiv) at a rate to maintain the temperature below 0°. When the addition of methanesulfonyl chloride was complete, the reaction mixture was stirred at 0° for an additional 0.5 hour, followed by warming to room temperature. The reaction mixture was then washed successively with water (6000 ml), 5% aqueous sodium bicarbonate (6000 ml), and brine (6000 ml). The organic phase was then dried over sodium sulfate (250 g) and filtered. Acetonitrile (3000 ml) was added to the filtrate. The volume was reduced by evaporation in vacuo to approximately 3000 ml, whereupon a precipitate formed. Additional acetonitrile (3000 ml) was added, and the volume was reduced to 2000 ml by evaporation in vacuo. The resulting suspension was cooled with an ice bath and stirred for 1.5 hours. The above-titled compound was filtered, washed with cold acetonitrile, and dried in vacuo at 50°.

PHYSICAL DATA:
m.p.: 172°–176°
NMR: ($^1$H, ppm, CDCl₃): 7.18–7.56 (m, 13H), 4.17 (br m, 1H), 3.55 (t, 1H, J=10.7 Hz), 3.41 (m, 1H), 2.75 (q, 1H, J=6.5 Hz), 2.56 (br m, 1H), 2.50 (d, 1H, J=6.3 Hz), 2.08 (m, 1H), 1.59 (m, 1H), 1.53 (d, 3H, J =6.5 Hz).

Example 2B: Alternative Procedure. The compound prepared by the method of Example 1 (278.0 g, 0.698 mol) was placed into a 5000-ml, 3-neck round bottom flask equipped with a mechanical stirrer, a thermocouple and an addition funnel with a nitrogen inlet. Anhydrous tetrahydrofuran (3000 ml) was added, followed by triphenylphosphine (228 g, 0.873 mol, 1.25 mol equiv.) and the resulting solution was stirred at room temperature under nitrogen. Diethyl azodicarboxylate (DEAD, 150.1 g, 0.873 mol) dissolved in tetrahydrofuran (100 ml) was added dropwise over a 5 hour period. The reaction mixture was stirred vigorously at room temperature overnight. The reaction mixture was then filtered through filter aid and silica gel (about 60 g), and washed with tetrahydrofuran (500 ml). The solvent was removed in vacuo, and the resulting semi-solid (715 g) was triturated with methanol (100 ml) and diethyl ether (600 ml), and refrigerated overnight. The solid was filtered, washed well with diethyl ether (3×100 ml), and dried. The solid (279.4 g, >100%) was triturated again with methanol (100 ml) and diethyl ether (500 ml), filtered, washed, and dried to yield 248.0 g that appeared to be >90% of the desired product by NMR.

Alternatively, after the first trituration, the thus obtained material could be recrystallized from isopropanol, approximately 20 ml/g. The following physical data are from a recrystallized sample:

PHYSICAL DATA:
m.p.: 184°–186°
IR: 2978 (m), 1638 (s), 1468 (s), 1455 (s), 1385 (s) cm$^{-1}$.
NMR: ($^1$H, ppm, CDCl₃): 7.18–7.56 (m, 13H), 4.17 (br m, 1H), 3.55 (t, 1H, J =10.7 Hz), 3.41 (m, 1H), 2.75 (q, 1H, J =6.5 Hz), 2.56 (br m, 1H), 2.50 (d, 1H, J =6.3 Hz), 2.08 (m, 1H), 1.59 (m, 1H), 1.53 (d, 3H, J =6.5 Hz).
($^{13}$C, ppm, CDCla): 168.6, 144.4, 141.6, 136.5, 132.8, 130.5, 128.6, 128.3, 127.3, 127.0, 126.7, 124.1, 69.9, 59.0, 38.6, 37.7, 34.5, 31.6, 23.6.
M.S.: m/e =380, 275, 261, 105, 77.
U.V.: $\lambda_{max}$=302 ($\epsilon$=8730), 272 ($\epsilon$=14000) in ethanol.
TLC: $R_f$=0.72 (SiO₂, hexane:ethyl acetate 1:1)=desired diastereomer
$R_f$=0.60 (SiO₂, hexane:ethyl acetate 1:1)=undesired diastereomer
$R_f$=0.28 (SiO₂, hexane:ethyl acetate 1:1)=amino alcohol
$R_f$=0.16 (SiO₂, hexane:ethyl acetate 1:1)=triphenylphosphine oxide
$R_f$=0.47 (SiO₂, hexane:ethyl acetate 1:1)=reduced DEAD
Visualization by UV and by iodine stain.

| Analysis: | C | H | N |
|---|---|---|---|
| theory | 82.07 | 6.37 | 7.36 |
| found | 81.79 | 6.34 | 7.28. |

$[\alpha]$= +32.75° (589 nm).
$[\alpha]$= +146.90° (365nm).

EXAMPLE 3

(2a-S,4-R,5-S)-1-Benzoyl-4,5-(S-1-phenylethyl)azirino-1,2,2a,3,4,5-hexahydrobenz[cd]indole From a reaction conducted according to the procedure of Example 1, filtrate (1000 ml) was collected from the first crop filtration. Thus the filtrate was a solution of (2a-S,4-S,5-S)-1-benzoyl-4-hydroxy-5-(S-1-phenylethyl)amino-1, 2,2a,3,4,5-hexahydrobenz[cd]indole in n-butanol, with amounts of S-1-phenylethylamine, of the product of Example 1, and of other compounds attendant to the reaction also in solution. To the solution was added solid carbon dioxide (200 g) in portions over a ten-minute period. Diethyl ether (200 ml) was added, and the suspension was stirred overnight. The resulting solid was filtered from the suspension and washed with diethyl ether until the effluent solvent was colorless. The solvent was removed from the filtrate in vacuo. To the residue was added water (500 ml), and the mixture was again evaporated to dryness in vacuo. The residue was taken up in water (800 ml). The mixture was distilled at ambient pressure until 500 ml of distillate was collected. The remaining mixture was cooled and combined with 1 N sodium hydroxide (100 ml). The aqueous solution was extracted twice with methylene chloride (300 ml, 100 ml), and the combined extracts were dried over sodium sulfate. The dessicant was filtered and washed with methylene chloride (100 ml), which was added to the filtrate. To the filtrate was added triethylamine (70 ml, 0.505 gmol). The resulting solution was cooled to $-5°$. Methanesulfonyl chloride (26 ml, 0.335 gmol) in solution in methylene chloride (75 ml) was added over 30 minutes, with the temperature maintained below $0°$. Additional portions of triethylamine (24 ml, 0.175 gmol) and methanesulfonyl chloride (13 ml, 0.175 gmol) solution (methylene chloride, 20 ml) were added. The reaction mixture was warmed to $20°$ and washed with water, saturated sodium bicarbonate, and brine (400 ml of each). The organic solution was dried over sodium sulfate, and the solvent was removed in vacuo. The residue was recrystallized from acetonitrile (100 ml). The crystallization mixture was stored at $0°$ for two days. The above-titled compound was filtered, washed (cold acetonitrile), and dried in vacuo at $50°$ and analyzed with the following results.

PHYSICAL DATA:
HPLC: 96.8% above-titled compound; no diastereomer detected.
IR: 3010 (m), 1636 (s), 1612 (s), 1596 (s), 1459 (s) 1398 (s) cm$^{-1}$.
NMR: ($^1$H, ppm, CDCls): 7.00–7.58(m, 13H), 4.21 (br m, 1H), 3.59 (t, 1H, J=10.7 Hz), 3.47 (m, 1H), 2.77 (br m, 2H), 2.37 (d, 1H, J=6.3 Hz), 2.24 (m, 1H), 1.71 (m, 1H), 1.47 (d, 3H, J=6.5 Hz).
($^{13}$C, ppm, CHCl$_3$): 168.6, 144.3, 141.2, 130.4, 128.5, 128.4, 128.3, 128.0, 127.4, 127.3, 127.0, 126.9, 70.0, 59.0, 39.3, 36.9, 31.6, 23.2.
M.S.: m/e=381, 277, 262, 105, 77.
U.V.: $\lambda_{max}$=294 ($\epsilon$=8780), 264 ($\epsilon$=11600) in ethanol.

| Analysis: | C | H | N |
|---|---|---|---|
| theory | 82.07 | 6.37 | 7.36 |
| found | 82.32 | 6.54 | 7.28 |

$[\alpha]$: $+34.4°$ (589 nm, Tetrahydrofuran)

$+152.7°$ (365 nm, Tetrahydrofuran)

EXAMPLE 4

1-benzoyl-4-hydroxy-5-(S-1-phenylethyl)amino-6-bromo-1,2,2a,3,4,5-hexahydrobenz[cd]indole A charge of (2a-RS,2a-$\alpha$,4-$\alpha$,5-$\alpha$)-1-benzoyl-4,5-epoxy-6-bromo-1, 2,2a,3,4,5-hexahydrobenz[cd]indole (1.07 g, 3 mmol) was placed into a 200-ml, 1-neck round bottom flask with n-butanol (100 ml). The S-1-phenylethylamine (1.55 ml, 1.45 g, 12 mmol) was added to the flask, and the flask was purged with nitrogen. The reaction mixture was heated to reflux for 24 hours. The solvent was removed in vacuo, with the addition of toluene aiding the removal of n-butanol. The residue was 1.88 g, 1.83 g of which was loaded onto a silica gel column (200 g) and eluted (69:20:11 toluene: ethyl acetate:triethylamine). Fractions were collected, analyzed by thin layer chromatography, and combined into two sections so that the two main components were isolated in substantially pure form.

EXAMPLE 4a (2a-R,4-R,5-R)-Diastereomer

The solvent was removed in vacuo to afford the earlier eluting compound (0.33 g).
PHYSICAL DATA:
X-RAY: Identified as (2a-R,4-R,5-R)-1-benzoyl-4-hydroxy-5-(S-1-phenylethyl)amino-6-bromo-1, 2,2a,3,4,5-hexahydrobenz[cd]indole.
m.p.: $239°$–$240.5°$

| Analysis: | C | H | N |
|---|---|---|---|
| theory: | 65.41 | 5.28 | 5.87 |
| found: | 64.64 | 5.38 | 5.79 |

$[\alpha]_D + 47.24°$ (589 nm)
$+307.09°$ (365 nm)

EXAMPLE 4b (2a-S,4-S,5-S)-Diastereomer

The solvent was removed in vacuo to afford the later eluting compound.
PHYSICAL DATA:
$[\alpha]$: $-13.17°$ (589 nm)
$-85.61°$ (365 nm)

Example 5

(2a-RS,2a-$\alpha$,4-$\alpha$,5-$\beta$)-1-Benzoyl-4-hydroxy-5-benzylamino-6-bromo-1, 2,2a,3,4,5-hexahydrobenz[cd]indole A charge of (2a-RS,2a-$\alpha$,4-$\alpha$,5-$\alpha$)-1-benzoyl-4,5-epoxy-6-bromo-1, 2,2a,3,4,5-hexahydrobenz[cd]indole (0.71 g, 2.0 mmol) was added to a 100 ml flask, to which was then added n-butanol (50 ml). The benzylamine (0.87 ml, 0.86 g, 8.0 mmol) was added to the flask. The reaction mixture was refluxed for three hours and analyzed by thin layer chromatography (silica, 70:15:15 toluene: ethyl acetate:triethylamine). The solvent was removed in vacuo to afford the above-titled product.
PHYSICAL DATA:
m.p. $178.5°$–$180.5°$

EXAMPLE 6

(2a-RS,2a-α,4-α,5-β)-1-Benzoyl-4-hydroxy-5-(n-propyl)amino-6-bromo-1,2,2a,3,4,5-hexahydrobenz[cd]indole A charge of (2a-RS,2a-α,4-α,5-α)-1-benzoyl-4,5-epoxy-6-bromo-1, 2,2a,3,4,5-hexahydrobenz[cd]indole (1.42 g, 4.0 mmol) was placed in a 100-ml, 3-neck round bottomed flask with n-butanol (50 ml) and 1-propylamine (2.05 ml, 1.48 g, 25.0 mmol). The reaction mixture was maintained at 80° for 17 hours. The solvent was removed in vacuo, with the addition of toluene (15 ml) added to aid in the removal of n-butanol, to afford a brown gum. The gum was dissolved in diethyl ether (25 ml). Following dissolution, a white precipitate formed. The solvent was removed in vacuo to afford a tan foam (1.81 g), which was loaded onto a column of silica gel (70 g, 230×400 mesh) and eluted with 1:1 tetrahydrofuran:toluene. Fractions of the eluent were collected and analyzed by thin layer chromatography (silica, 42:42:16: ethyl acetate:toluene:triethylamine). The fractions containing the desired product were combined, and the solvent was removed in vacuo to afford a tan foam (1.51 g).

EXAMPLE 7

1-benzoyl-4-hydroxy-5-(R-1-phenylethyl)amino-1,2,2a,3,4,5-hexahydrobenz[cd]indole A charge of (2a-RS,2a-α,4-α,5-α)-1-benzoyl-4,5-epoxy-1, 2,2a,3,4,5-hexahydrobenz[cd]indole (0.36 g, 1.00 mmol) was added to a 100-ml, 1-neck round bottom flask. The n-butanol (50 ml) was added to the flask, followed by the R-1-phenylethylamine (0.65 ml, 0.606 g, 5.0 mmol). The reaction mixture was refluxed for approximately 72 hours. The reaction mixture was analyzed by thin layer chromatography (silica, 42:42:16 ethyl acetate:toluene: triethylamine), which showed two products. The solvent was removed in vacuo to afford a residue (0.60 g). The residue was loaded onto a chromatography column (silica, 60 g, 230×400 mesh) and eluted with 42:42:16 ethyl acetate:toluene:triethylamine. Fractions were collected, analyzed by thin layer chromatography, and combined into two sections so that the two main components were isolated in substantially pure form.

EXAMPLE 7a (2a-S,4-S,5-S)-Diastereomer

The solvent was removed in vacuo to afford the earlier eluting compound as a white foam (0.078 g).
PHYSICAL DATA:
[α]: −40.78° (589 nm, tetrahydrofuran, 10.3 mg/ml)
−269.9° (365 nm, tetrahydrofuran, 10.3 mg/ml)

| Analysis: | C | H | N |
| --- | --- | --- | --- |
| theory | 65.41 | 5.28 | 5.87 |
| found | 66.02 | 5.56 | 6.65 |

EXAMPLE 7b (2a-R,4-R,5-R)-Diastereomer

The solvent was removed in vacuo to afford the later eluting compound as a tan oil (0.107g).
PHYSICAL DATA:

NMR: Identified as above titled compound by comparison with compound of Example 4b.
[α]: +8.86° (589 nm, tetrahydrofuran, 10.16 mg/ml)
+54.14° (365 nm, tetrahydrofuran, 10.16 mg/ml)

| Analysis: | C | H | N |
| --- | --- | --- | --- |
| theory | 65.41 | 5.28 | 5.87 |
| found | 66.32 | 5.40 | 5.50 |

EXAMPLE 8

(2a-R,4-S)-1-benzoyl-4-amino-1,2,2a,3,4,5-hexahydrobenz[cd]indole

A 500-mL, 3-neck round bottom flask equipped with a mechanical stirrer, a thermocouple and a condenser topped with a three-way gas/vacuum adapter was charged with the compound prepared by the method of Example 2 (19.0 g, 0.050 mole) followed by the addition of a pre-cooled (−5°) solution of glacial acetic acid:methanol (170 ml:70 ml). The resulting solution was stirred at −5° and the atmosphere was replaced with nitrogen. A suspension of 10% Pd/C (8.50 g) in glacial acetic acid (40 ml) was added, and the atmosphere was replaced with hydrogen at about atmospheric pressure and the reaction mixture was stirred at this temperature for 2 hours. The reaction mixture was then stirred at 55° for an additional 6 hours to complete the second reduction, namely cleavage of the chiral phenylethyl auxiliary. The reaction mixture was cooled to room temperature, filtered through filter aid, washed with acetic acid (5×50 mL) and the filtrate was concentrated in vacuo at 30° C. To the gummy residue was added methylene chloride (200 mL) and 1N hydrochloric acid (200 mL). The layers were separated, and the organic phase was extracted with another portion of 1N hydrochloric acid (2×100 mL). The combined aqueous phase was made basic with 5N sodium hydroxide and exhaustively extracted with methylene chloride (200 ml +2×100 mL). The combined organic phase was dried over brine, then sodium sulfate. Removal of the solvent in vacuo afforded 12.46 g of the desired primary amine which crystallized upon standing. Recrystallization from either isopropanol or 50% aqueous ethanol afforded short needle-like crystals.
PHYSICAL DATA:
m.p.: 147°–150°.
IR: 1225 (w), 1396 (s), 1457 (s), 1488 (m), 1597 (m), 1612 (s), 1637 (s), 3009 (m) cm$^{-1}$.
NMR: ($^1$H, ppm, CDCl$_3$): 7.38–7.57 (m, 5H), 6.99 (m, 1H), 6.78 (m, 2H), 4.25 (br m, 1H), 3.62 (t, 1H, J=11.5 Hz), 3.29 (m, 2H), 3.12 (dd, 1H, J=6.1, 16.7 Hz), 2.39 (dd, 1H, J=10.3, 16.7 Hz), 2.17 (m, 1H), 1.49 (br s, 2H), 1.31 (q, 1H, J=11.5 Hz).
($^{13}$C, ppm, CDCl$_3$): 168.5, 141.4, 136.6, 133.3, 132.6, 130.7, 130.1, 128.8, 128.1, 127.7, 127.6, 127.1, 123.1, 122.6, 58.2, 48.6, 37.3, 37.2, 36.9.
M.S.: m/e =278, 261, 235, 130, 105, 77.
U.V.: λ$_{max}$=291 (ε=8150), 266 (ε=10600) in ethanol.
TLC: R$_f$=0.19 (SiO$_2$, CH$_2$Cl$_2$:methanol 4:1)=desired product.
R$_f$=0.41 (SiO$_2$, ethyl acetate:hexanes 1:1)=aziridine.
R$_f$=0.86 (SiO$_2$, CH$_2$Cl$_2$:methanol 4:1)=secondary amine.
R$_f$=0.13 (SiO$_2$, ethyl acetate:hexanes 1:1)=secondary amine.

Visualization by UV and by iodine stain.

| Analysis: | C | H | N |
|---|---|---|---|
| theory | 77.67 | 6.52 | 10.06 |
| found | 77.76 | 6.55 | 9.61 |

$[\alpha] = +57.43$ (589 nm).
$[\alpha] = +341.58$ (365 nm).

We claim:

1. A stereospecific process for preparing a substantially pure enantiomer of the compound of the formula

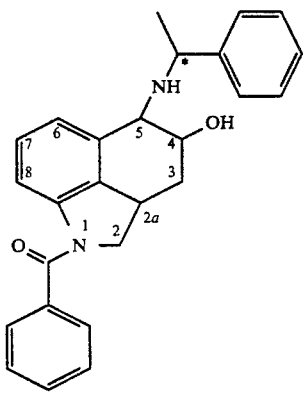

wherein
i) the 2-carbon is in the R configuration, the 4 carbon is in the R configuration, the 5 carbon is in the R configuration; and the carbon marked * is in the S configuration; or
ii) the 2-a carbon is in the S configuration, the 4 carbon is in the S configuration, the 5 carbon is in the S configuration, and the carbon marked * is in the R configuration; or
iii) the 2-a carbon is in the R configuration, the 4 carbon is in the S configuration, the 5 carbon is in the S configuration, and the carbon marked * is in the R configuration; or
iv) the 2-a carbon is in the S configuration, the 4 carbon is in the configuration, the 5 carbon is in the R configuration, and the carbon marked * is in the S configuration;

which process comprises:
1) reaction of a mixture of substantially the α-isomers or substantially the β-isomers of the compound of the formula

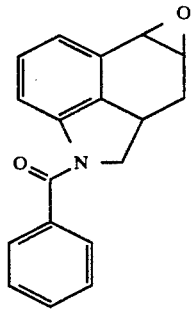

with a substantially pure optical isomer of 1-phenylethylamine, in n-butanol, to form a mixture of enantiomers of said compound;
2) selective crystallization of one of said enantiomers; and
3) isolation of the crystallized enantiomer.

2. A process of claim 1 which comprises the reaction of a mixture of substantially the β-isomers of Formula IV with the substantially pure enantiomer S-1-phenylethylamine.

3. A process of claim 1 which comprises the reaction of a mixture of substantially the β-isomers of Formula IV with the substantially pure enantiomer R-1-phenylethylamine.

4. A process of claim 1 which comprises the reaction of a mixture of substantially the α-isomers of Formula IV with the substantially pure enantiomer S-1-phenylethylamine.

5. A process of claim 1 which comprises the reaction of a mixture of substantially the α-isomers of Formula IV with the substantially pure enantiomer R-1-phenylethylamine.

6. The process of claim 1 wherein said selective crystallization is accomplished from n-butanol.

* * * * *

UNITED STATES PATENT AND TRADEMARK OFFICE
CERTIFICATE OF CORRECTION

PATENT NO.   :   5,212,319

DATED        :   May 18, 1993

INVENTORS    :   Thomas J. Kress, et al.

It is certified that an error appears in the above-identified patent and that said Letters Patent is hereby corrected as shown below:

Claim 1, column 19, line 46, "carbon is in the configuration," should read --carbon is in the R configuration,--.

Signed and Sealed this

Fifth Day of April, 1994

Attest:

BRUCE LEHMAN

*Attesting Officer*   *Commissioner of Patents and Trademarks*